(12) United States Patent
Lanin et al.

(10) Patent No.: US 8,617,121 B2
(45) Date of Patent: Dec. 31, 2013

(54) DRUG DELIVERY DEVICE

(75) Inventors: Irina Lanin, Frankfurt am Main (DE); Bernhard Forys, Frankfurt am Main (DE); Alastair Clarke, Cheshire (GB); Matthew Ekman, Cheshire (GB); Kirsten Goode, Frankfurt am Main (DE); Michael Heald, Cheshire (GB); John Hiles, Cheshire (GB); Chris Smith, Cheshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/202,467

(22) PCT Filed: Mar. 4, 2010

(86) PCT No.: PCT/EP2010/052787
§ 371 (c)(1),
(2), (4) Date: Jan. 25, 2012

(87) PCT Pub. No.: WO2010/100242
PCT Pub. Date: Sep. 10, 2010

(65) Prior Publication Data
US 2012/0116320 A1    May 10, 2012

(30) Foreign Application Priority Data
Mar. 5, 2009    (EP) .................................... 09003179

(51) Int. Cl.
*A61M 5/32*    (2006.01)
*A61M 5/00*    (2006.01)
*A61M 5/315*    (2006.01)

(52) U.S. Cl.
USPC ............................ 604/195; 604/187; 604/218

(58) Field of Classification Search
USPC ........................... 604/110, 187, 195–196, 218
See application file for complete search history.

(56) References Cited

U.S. PATENT DOCUMENTS

| | | | |
|---|---|---|---|
| 2006/0084918 A1* | 4/2006 | Lou | 604/110 |
| 2006/0189932 A1 | 8/2006 | Yang et al. | |
| 2007/0066936 A1 | 3/2007 | Lam | |
| 2008/0255514 A1 | 10/2008 | Crapser | |

FOREIGN PATENT DOCUMENTS

| | | |
|---|---|---|
| WO | 03095004 A1 | 11/2003 |
| WO | 2007123826 A2 | 11/2007 |

OTHER PUBLICATIONS

Form PCT/IB/326, Notification Concerning Transmittal of International Preliminary Report on Patentability.

* cited by examiner

*Primary Examiner* — Nicholas Lucchesi
*Assistant Examiner* — Rebecca E Eisenberg
(74) *Attorney, Agent, or Firm* — McDonnell Boehnen Hulbert & Berghoff LLP (57) ABSTRACT

Drug delivery device, comprising a body unit having a first opening and a second opening, a plunger arranged such that its distal end is positioned inside the body unit, wherein the plunger is moveable in the distal direction with respect to the body unit, a needle assembly, with a proximal end and a distal end comprising a needle, wherein the proximal end of the needle assembly and the distal end of the plunger are configured such that they can get into a vacuum connection.

13 Claims, 8 Drawing Sheets

DRUG DELIVERY DEVICE

CROSS REFERENCE TO RELATED APPLICATIONS

The present application is a 35 U.S.C. 371 National Application of PCT/EP2010/052787 filed Mar. 4, 2010, which claims priority to European Patent Application No. 09003179.0 filed Mar. 5, 2009, the entire contents of which are incorporated entirely herein by reference.

The invention relates to a drug delivery device wherein the proximal end of a needle assembly and the distal end of a plunger are configured such that they can get into a vacuum connection.

One problem of existing drug delivery devices, for example safety syringes which have a retractable needle, is how to connect the plunger of the syringe with the needle or needle assembly so that the needle is retractable by the plunger.

Many drug delivery devices, especially safety syringes which have a retractable needle, are constructed in a way that if the plunger is pressed onto the needle or needle assembly, one part snaps into the other and both parts are mechanically connected. In this case, the inner side of the plunger and the inner side of the needle assembly have to be formed in a key-lock principle or snap-over principle, which is mechanically complex.

One embodiment of the invention is directed to a drug delivery device comprising: a body unit having a first opening and a second opening, a plunger arranged such that its distal end is positioned inside the body unit, wherein the plunger is moveable in the distal direction with respect to the body unit, a needle assembly, with a proximal end and a distal end comprising a needle, wherein the proximal end of the needle assembly and the distal end of the plunger are configured such that they can get into a vacuum connection.

In conjunction with this invention it should be understood by "vacuum connection" that the pressure in a defined region formed by given elements is reduced compared to the pressure surrounding of this elements.

The drug delivery devices, which for example could be a syringe, preferably a safety syringe, comprise a body unit. The body unit could be a main body of the drug delivery device, a cartridge for an auto-injector or pen-type drug delivery device for example which could be formed, for example, in a cylindrical way. The body unit has two openings, a first opening and a second opening, which are preferably positioned at opposite ends of the body unit. The drug delivery device further comprises a plunger which is arranged with respect to the body unit so that it can be moved in the distal direction, for example by pressing on the proximal end of the plunger which is positioned outside of the body unit. The drug delivery device further comprises a needle assembly, whereby the needle itself is a part of the needle assembly. The needle comprises an outer surface and an inner surface, whereby the inner surface is forming a channel, through which liquids could flow through. The needle assembly has a proximal end and a distal end wherein the proximal end of the needle assembly is located inside the body unit. The proximal end of the needle assembly and the distal end of the plunger are configured such that they can get into a vacuum connection. Vacuum connection means that if these two parts are pushed together, there is an interspace between these two parts and the pressure inside this interspace is reduced compared to the pressure outside of these two parts and the interspace. The plunger is configured to get into a vacuum connection means that the plunger itself is formed in a way to get into a vacuum connection or that the plunger comprises an additional part, which is able to get into the vacuum connection.

In another embodiment, the distal end of the plunger has a first connecting element, which means that the distal end of the plunger itself could be formed as a connecting element or that the connecting element is attached to the distal end of the plunger.

In another embodiment, the distal end of the plunger has a first connecting element comprising a flexible material.

This first connecting element is especially formed to get into a vacuum connection with the proximal end of the needle assembly. For this, the first connecting element is made of a flexible material, which could be, for example, rubber or a material which comprises rubber. This first connecting element is formed in a way that at least parts of the element are deformable.

In another embodiment, the needle assembly has a second connecting element located at its proximal end.

The proximal end of the needle assembly is located inside the body unit and directed towards the plunger. Preferably, the second connecting element is directed towards the first connecting element of the plunger. Preferably, the first and the second connecting elements are matched to each other in their forms and their materials. Therefore these two connecting elements are able to get into a strong vacuum connection so that the two parts, the needle assembly and the plunger, could be connected in a strong way without any snap mechanism.

In another embodiment at least one of the first and the second connecting elements is a bung.

In another embodiment, the first connecting element is a bung.

Bungs have the ideal requirements to go into a vacuum connection. They can be made of a flexible material, can be deformable and can be formed in a way that they have a concave surface.

In another embodiment, the second connecting element is a bung.

Bungs have the ideal requirements to get into a vacuum connection. They are particularly able to get into a vacuum connection with another bung.

In another embodiment at least one of the first and second connecting elements is elastic and concave towards the respective other element.

In another embodiment, the first connecting element is formed concavely at the side which gets into the vacuum connection.

The concavely formed first connecting element is able to get into a vacuum connection, for example with other connecting elements which could be formed: concavely, convex or planar. The concave form is ideal in combination with a flexible material for a connecting element to get into a vacuum connection.

In another embodiment, the second connecting element is elastic and concave towards the respective other element.

The second connecting element could be formed in a flexible and concave way like, for example, the first connecting element. By pressing these two connecting elements together, an interspace is formed between these two connecting elements. The pressure in the interspace can be observed to be reduced compared to the surrounding of the two connecting elements by at least partly removing some of the fluid, for example liquid and/or air, from the interspace.

In another embodiment, one of the first and the second connecting element is elastic and convex towards the respective other element.

The second connecting element could also be formed convex, especially in the case that the first connecting element is formed concavely. Also, the other way round, it is possible that the first connecting element is formed convex and the second connecting element is formed concave. The combination of a convex and a concave connecting element also makes it possible that if both connecting elements are pressed onto each other, that they get into a vacuum connection.

In another embodiment, at least one of the first and the second connecting elements is rigid and planar.

It is especially possible for the second connecting element to be rigid and planar if the first connecting element is formed concavely and made of a flexible material. So if the concavely formed first connecting element is pressed on the rigid and planar second connecting element and the first connecting element is made of a flexible material, the first connecting element could change its form into a planar or nearly planar form. By pressing the convex formed first connecting element onto the rigid and planar second connecting element, the volume of the interspace between the two connecting elements is reduced. If at least a part the fluid, for example liquid and/or air, is removed from the interspace, for example through the needle or by leaking past the seal formed between the connecting elements then the pressure inside the interspace is reduced as the elastic nature of one or both connecting elements causes the interspace to tend to return to its original volume. Therefore, the pressure inside the interspace of the two connecting elements is reduced compared to the pressure outside the interspace and the surrounding of the two connecting elements and therefore, a vacuum connection is formed.

In another embodiment, the first and the second connecting elements, by being pressed together, get into a vacuum connection combining the needle assembly with the plunger.

By being pressed on each other, the two connecting elements get into a vacuum connection, whereby the needle assembly and the plunger are combined without a snap mechanism like a key-lock-mechanism. So the needle assembly and the plunger could be connected without forming complicated components which comprise complicated forms at the ends. Preferably the vacuum connection is formed between two bungs.

In another embodiment, the needle assembly is configured to be at least partly drawn back into the body unit, when the plunger is retracted.

The needle assembly is configured in a way, that the resistance of the needle assembly to the retracting force is lower than the force of the vacuum connection.

Therefore the needle and the needle assembly could be drawn back into the body unit, for example after the final use of the drug delivery device, whereby the risk of injury, for example at the distal end of the needle, is reduced.

In another embodiment, the drug delivery device is configured such that the needle does not move with respect to the body unit, when the needle assembly is in vacuum connection with the plunger and the needle assembly has been drawn back into the device.

The needle assembly and the needle could be arranged inside the body unit, for example, in such a way that once in the drawn back position they are not able to move in a distal direction. The needle and the needle assembly should not be able to move in the distal direction with respect to the body unit when the plunger is further pressed on the proximal end of the needle assembly. This reduces the risk of injury, for example needlestick injuries.

In another embodiment, the proximal end of the needle is aligned with the second connecting element.

If the proximal end of the needle is aligns with the second connecting element, for example, a planar second connecting element could be formed. This planar second connecting element can now easily go into a vacuum connection, for example with a first connecting element which is formed concavely.

In another embodiment, the proximal end of the needle protrudes from the second connecting element in the direction of the plunger.

Also, if the proximal end of the needle assembly is formed in this way, it is possible that the first connecting element, which is located at the inner side of the plunger, is able to get into a vacuum connection with the second connecting element. For example, the first connecting element is able to get into the vacuum connection with the second connecting element directly with that part of the needle, which protrudes from the second connecting element, or the first connecting element could be able to form a vacuum connection with those parts of the second connecting element, which are located at the outer side which is close to the body unit.

In another embodiment, the first connecting element is configured to seal hermetically with the proximal end of the needle.

The first connecting element could be formed in a way that it could get into a vacuum connection directly with the end of the needle or it could be formed in a way that it gets into a vacuum connection with the second connecting element and additionally hermetically seals with the end of the needle. If the first connecting element is configured in a way that it seals hermetically with the end of the needle, it is not possible that gases like, for example, air could get from the outside through the needle channel into the interspace between the first and the second connecting element. If, for example, it would be possible for air to get into the interspace between the two connecting elements, the pressure in the interspace between the two connecting elements would increase and the strength of the vacuum connection would decrease.

In another embodiment, the first connecting element is configured to get into a vacuum connection with the second connecting element.

The first and the second connecting elements are matched to each other so that it is possible for these two elements to get into a vacuum connection.

In another embodiment, the needle unit is not detachable with respect to the body unit.

Not detachable with respect to the body unit means that the needle unit cannot be removed from the body unit but it also means that a needle unit cannot be attached to the body unit. The needle unit and the body unit therefore form one part but it is possible to move the needle unit with the needle with respect to the body unit. This makes it, for example, possible that after the needle unit and the plunger are connected with the vacuum connection, the needle unit could be drawn back into the body unit by means of the plunger.

In another embodiment, the second connecting element is initially located in a position in contact with the inner surface of body unit and moves in a proximal direction to a position where it is no longer in contact with the inner surface of body unit.

In another embodiment, wherein the second connecting element is initially located in a position in contact with the inner surface of body unit and is moveable in proximal direction with respect to the body unit to a position where it is no longer in contact with the inner surface of the body unit.

If the body unit has a section with reduced internal diameter in which the second connection element is located in the initial position and the second connection element moves proximally into the body unit it can reach a position where it is no longer in contact with the body unit. The diameter of the second connection element is smaller than that of the main diameter of the body unit. Therefore, once the second connection element has ceased to contact the section of reduced internal diameter, the body unit offers no further resistance to the proximal movement of the second connection element and the needle.

In a further embodiment the drug delivery device comprises a medicament. The medicament could be pre-filled in a cartridge or, if the drug delivery device is designed as a syringe, pre-filled in the syringe.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly (A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38[Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane such as hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The following figures are for illustrating some embodiments of the drug delivery device of the invention.

Figure 1:
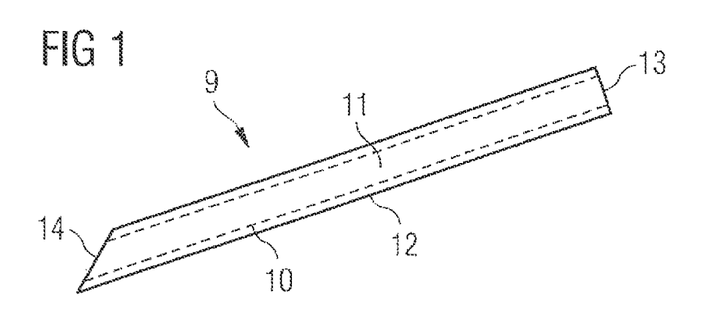
FIG. 1 shows a schematic cross-section of an embodiment of the needle.

FIG. 1 shows schematically the cross-section of an embodiment of the needle 9. The needle 9 comprises an inner surface 10 which is forming a channel 11. Furthermore, the needle 9 comprises an outer surface 12, a proximal end 13 and a distal end 14. The distal end 14 is preferably acuminated. The proximal end 13 of the needle is preferably flat.

Figure 2:
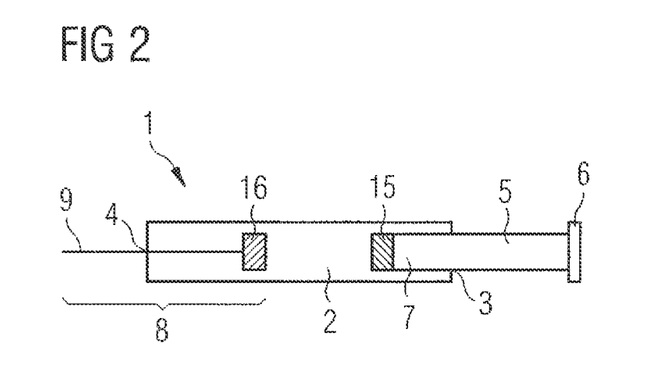
FIG. 2 shows a schematic cross-section of an embodiment of the drug delivery device.

FIG. 2 shows schematically the cross-section of one embodiment of the drug delivery device 1. The drug delivery device 1 comprises a body unit 2 and a needle assembly 8. The needle assembly 8 is positioned with respect to the body unit 2 in a way that the second connecting element 16 which is arranged at the proximal end of the needle assembly 8 is located inside the body unit 2 and the needle 9 exits the body unit 2 through the second opening 4. The drug delivery device 1 further comprises a plunger 5 whereby the distal end 7 is positioned inside the body unit 2 and the proximal end 6 of the plunger 5 is positioned outside the body unit 2. The plunger 5 comprises a first connecting element 15 located at its distal end 7. So the first connecting element 15 and the second connecting element 16 are arranged in a way that they are facing each other. The plunger 5 is movable to the distal direction with respect to the body unit 2 so that the first connecting element 15 can be moved towards the second connecting element 16. Furthermore, the first connecting element 15 could be pressed onto the second connecting element 16. By pressing these two connecting elements 15, 16, these two connecting elements can get into a vacuum connection. After getting into the vacuum connection, the plunger now can be moved into a proximal direction with respect to the body unit and could draw back the needle assembly 8 into the body unit 2.

Figure 3A:
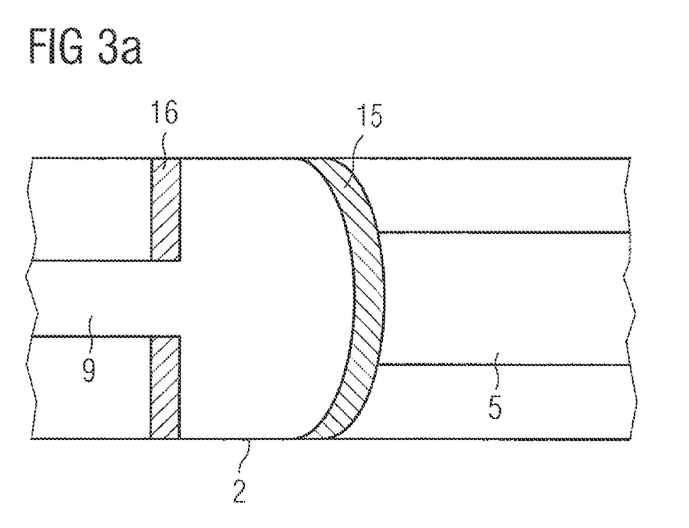
FIGS. 3a/b show a schematic cross-section of an embodiment of a cutout of the drug delivery device.
Figure 3B:
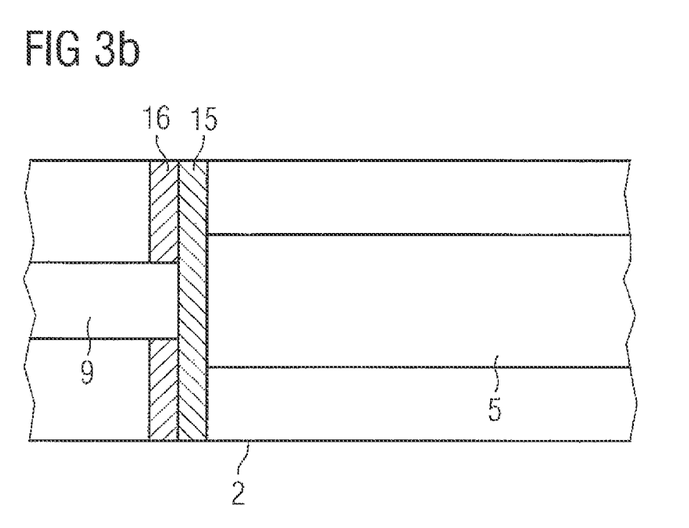

FIGS. 3a/b show a schematic cross-section of an embodiment of the drug delivery device in a section. The two figures show the body unit 2, a section of the needle 9 on the left side and a section of the plunger 5 on the right side. The second connecting element 16, which is located at the proximal end of the needle 9, is shown. The second connecting element 16 is formed planar in this embodiment. The proximal end of needle 9 aligns with the second connecting element 16 in this embodiment. The first connecting element 15, which is located at the inner side of the plunger 5, is formed concavely in this embodiment. The first connecting element 15 is preferably made of a flexible material, it could be a bung for example. The FIG. 3b shows the situation when then plunger 5 is moved to the distal direction with respect to the body unit 2. Now, the first connecting element 15 and the second connecting element 16 are in contact with each other and the proximal end of the needle 9 is hermetically or nearly hermetically sealed by a face seal to the surface of the first connecting element 15. This forms a vacuum connection between the first and second connecting elements 15,16. Therefore, the plunger 5 and the needle assembly 8 are now engaged by means of the vacuum connection.

Figure 4A:
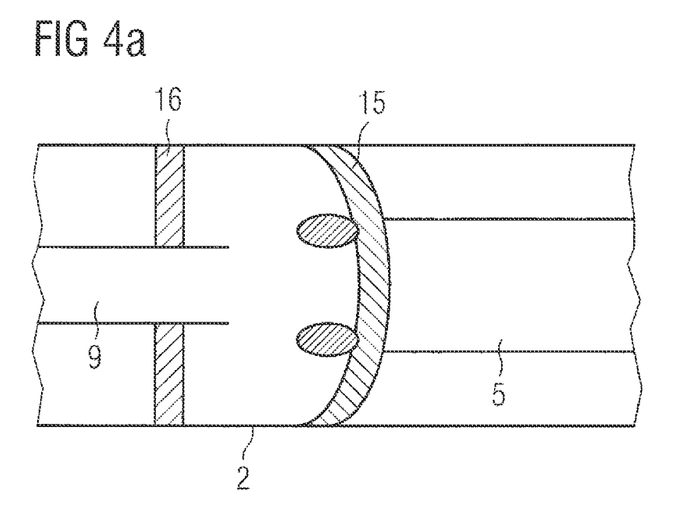
FIGS. 4a/b show a schematic cross-section of another embodiment of the drug delivery device in a cutout.
Figure 4B:
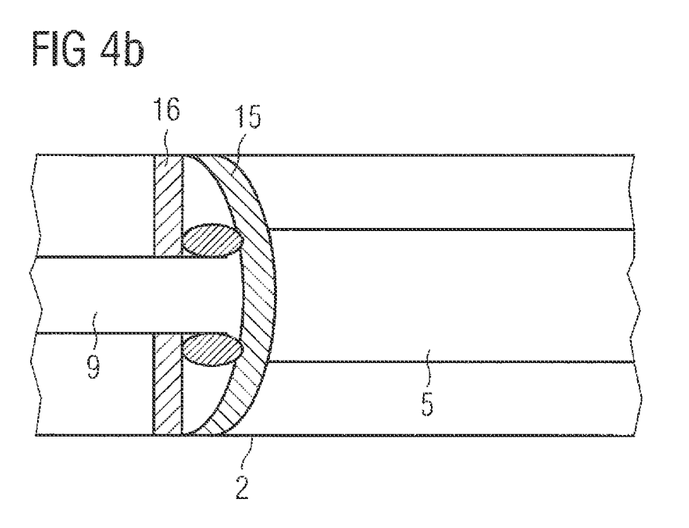

The FIGS. 4a/b show a cross-section of another embodiment of the drug delivery device 1 in a section. The section shows, like the previous FIGS. 3a/b the body unit 2, the proximal end of the needle assembly with the needle 9 on the left side and the distal end of the plunger 5 at the right side. In this embodiment, the needle 9 protrudes from the second connecting element 16. The first connecting element 15 is formed in a way, that it is able to seal hermetically with the end of the needle 9. FIG. 4b shows the situation when the plunger 5 is moved to the distal direction with respect to the body unit 2. The two connecting elements 15, 16 are now in contact with each other. The inner part of the first connecting element 15 seals hermetically or nearly hermetically with the end of the needle 9. The outer part of the first connecting element 15 forms a vacuum connection with the second connecting element 16. The inner part of the first connecting element 15 makes sure that no gases, for example air, are moved from the outside through the needle 9 into the interspace between the two connecting elements 15, 16 which could increase the gas pressure between the two connecting elements 15, 16, and therefore decrease and weaken the vacuum connection. The formation of the hermetic or nearly hermetic seal between the end of the needle 9 and first connecting element 15 may be achieved by means of an inner part of the connecting element 15 being designed to receive the end of the needle 9, as shown in FIG. 3b, or by the end of the needle 9 piercing into the surface of the first connecting element 15.

There are also embodiments possible, where the needle 9 aligns with the second connecting element 16.

The FIGS. 5a to 5f show a schematic cross-section of an embodiment of the drug delivery device 1, which is a syringe, in six different steps of use.

Figure 5A:
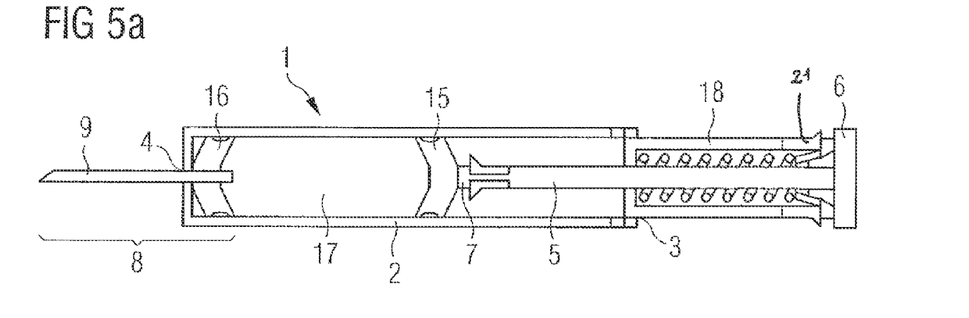
FIG. 5a-f show a schematic cross-section of an embodiment of the drug delivery device in six different steps of use.

FIG. 5a shows a schematic cross-section of an embodiment of the drug delivery device 1 comprising a body unit 2 with a first opening 3 at the proximal side and a second opening 4 at the distal side. The drug delivery device 1 further comprises a needle assembly 8 comprising a needle 9 and a second connecting element 16. The drug delivery device 1 further comprises a plunger 5 with a distal end 7 and a proximal end 6. The proximal part of the plunger 5 is surrounded by a sleeve 18. The sleeve 18 comprises snap arms 21. There is a spring 19, which is pre-compressed in a stressed condition, located between the sleeve 18 and the plunger 5. The plunger 5 comprises at its distal end 7 a first connecting element 15. A liquid 17 is located between the first connecting element 15 and the second connecting element 16, for example in the case of a pre-filled syringe the liquid could include a drug. The FIG. 5a shows the drug delivery device, which could be for example a syringe, preferably a safety syringe, in its starting position.

Figure 5B:
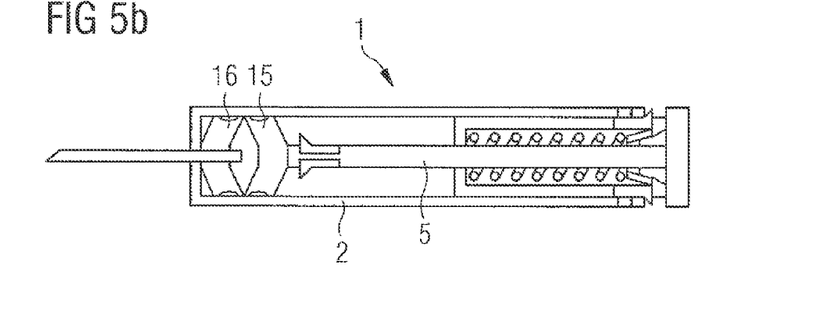

FIG. 5b schematically shows a cross-section of the drug delivery device 1 in an intermediate step of the use of the drug delivery device which is shown in FIG. 5a. In FIG. 5b the plunger 5 is pushed in the distal direction with respect to the body unit 2. The plunger 5 is pushed so far that the first and the second connecting elements 15, 16 come into first contact.

Figure 5C:
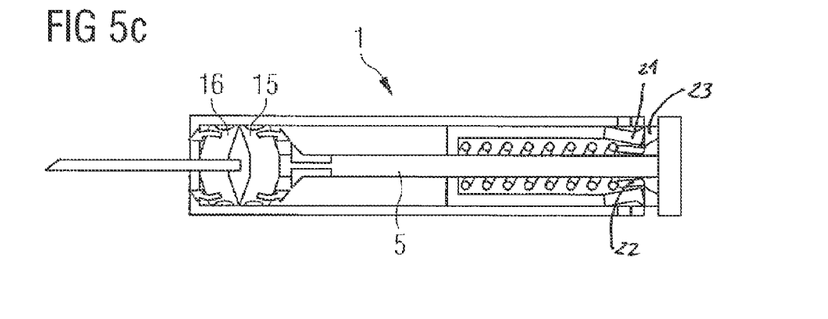

FIG. 5c schematically shows the cross-section of the drug delivery device 1 in an intermediate step of use of the drug delivery device 1 which is shown in FIG. 5a. By further pushing the plunger 5 into the distal direction now the first and the second connecting elements 15, 16 start to deform. The facing surfaces of the first and the second connecting element 15, 16 which were previously concave are now being pressed to the distal direction in the case of the second connecting element 16 and to the proximal direction in the case of the first connecting element 15. The sleeve snap arms 21 push the plunger rod latch arms 22 inwards. The plunger rod latch arms 22 snap inwards over sleeve latch features 23.

Figures 5D, 5E:
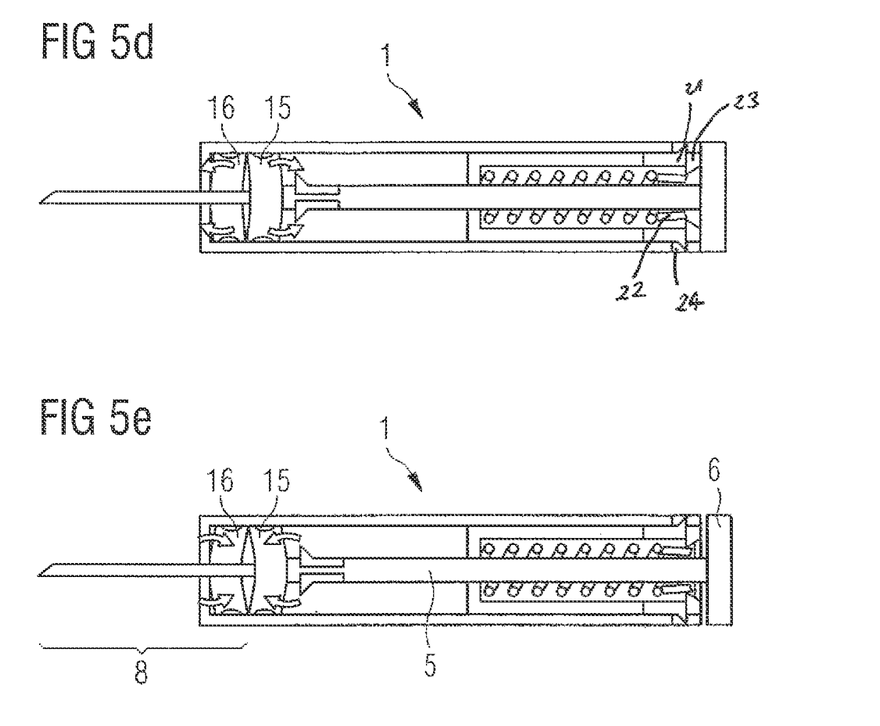

FIG. 5d schematically shows a cross-section of the drug delivery device 1 in an intermediate step of the drug delivery 1 which is shown in FIG. 5a. The first and the second connecting element 15, 16 have now been pressed so far together that they come into a vacuum connection. The proximal end of the needle 9 pierces into the surface of the first connecting element 15 forming a hermetic or nearly hermetic seal. The sleeve snap arms lock into recesses of the body unit 2. Therefore the sleeve 18 is now connected to the body unit 2 and can no longer move with respect to the body unit 2. The plunger rod latch arms 22 of the plunger 5 remain in their deformed condition clear of the sleeve latch features 23.

FIG. 5e schematically shows a cross-section of the drug delivery device 1 in a further intermediate step of the use of the drug delivery device which is shown in FIG. 5a. By removing the pressure from the proximal end 6 of the plunger 5 now the first and the second connecting elements 15, 16 tend to return to their original concave form which would increase the volume in the interspace between the first and second connecting elements 15, 16. The first and the second connecting elements 15, 16 are still in contact in their border area and hermetically sealed inside against the surroundings. The proximal end of the needle 9 remains embedded in, and hermtically or nearly hermetically sealed to, the surface of the first connecting element 15. Because of this no gas or liquid is able to enter the interspace between the first and the second connecting elements 15, 16. Therefore, the tendency of the first and the second connecting elements 15, 16 to return to their original concave form causes a vacuum connection to form between them. Over this vacuum connection the needle assembly 8 is connected to the plunger 5.

Figure 5F:
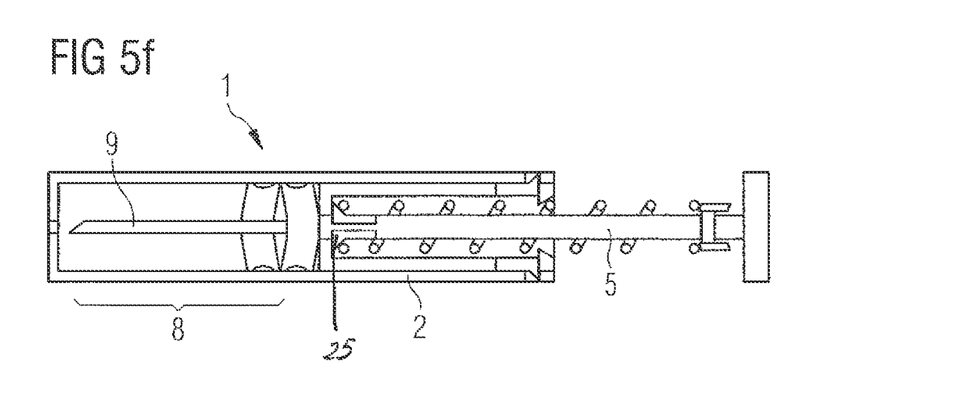

FIG. 5f schematically shows a cross-section of the drug delivery device in a further step of use of the drug delivery device, which is shown in FIG. 5a. In FIG. 5f the plunger 5 has been drawn back with respect to the body unit 2 into the proximal direction by the spring 19, which was pre-stressed. The needle 9 has been drawn back so far that the whole needle 9 is located inside the body unit 2. In the end position the distal end 7 contacts to the sleeve 18. The plunger rod snap arms 25 deflect inwards as they pass through a hole in the distal end surface of sleeve 18. Once the plunger rod snap arms 25 are clear of the hole in sleeve 18 the plunger rod snap arms 25 flex outwards to lock the plunger 5 in the rearwards position relative to the sleeve 18 and prevents the needle 9 from moving into the distal direction anymore. Now in the end position the whole needle assembly 8 and the whole needle 9 are located inside the body unit 2. Now the user of the drug delivery device 1 is protected from being injured by the needle 9.

Figure 6A:
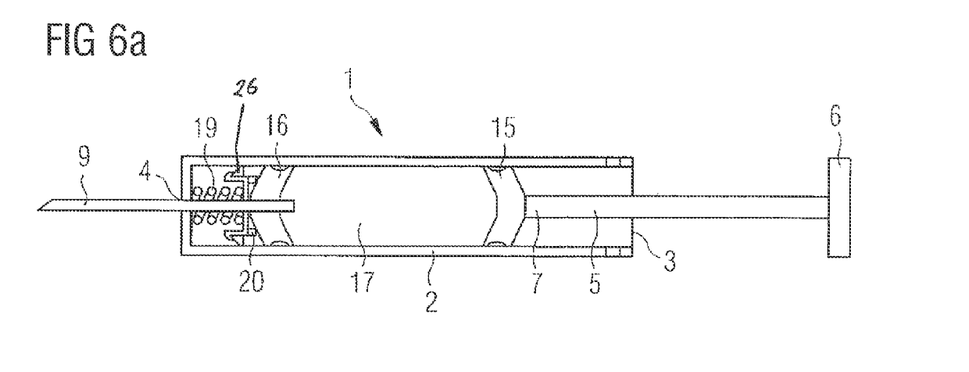
FIG. 6a-c show a schematic cross-section of another embodiment of the drug delivery device in three different steps of use.
Figure 6B:
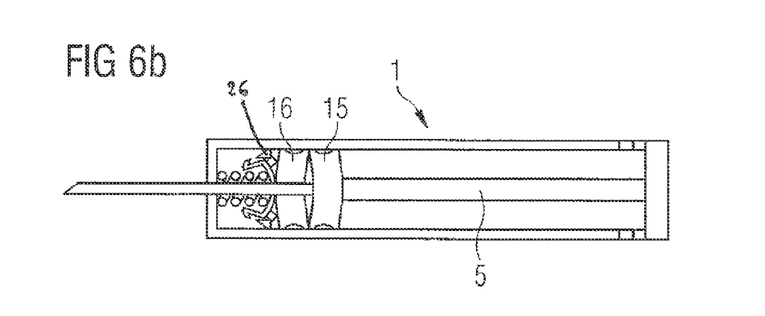
Figure 6C:
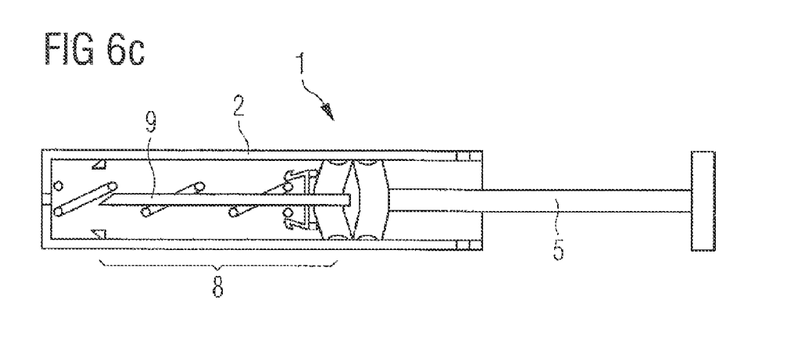

FIGS. 6a to 6c show a schematic cross-section of another embodiment of the drug delivery device 1 in three different steps of use.

An embodiment of the drug delivery device 1 which is shown in FIG. 6a comprises a body unit 2 with a second opening at its distal end and a first opening 3 at its proximal end. The drug delivery device further comprises a needle assembly 8 comprising a needle 9 and a second connecting element 16. Further the drug delivery device 1 comprises a plunger 5 with a proximal end 6 and distal end 7. At the distal end 7 of the plunger the first connecting element 15 is located. Between the first and the second connecting element 15, 16 a liquid 17 is located which could, for example contain a drug. Between the second connecting element 16 and the second opening 4 a spring 19 is located. Between the spring 19 and the second connecting element 16 there is a spring retainer 20, which keeps the spring 19 in a pre-compressed stressed state until the spring retainer 20 is unlatched. The spring retainer 20 is held in position relative to the body unit 2 by engagement of latch features of the spring retainer 20 with protrusions 26 from the inside surface of the body unit 2.

FIG. 6b schematically shows a cross-section of the drug delivery device in an intermediate step of use. In this step of use the plunger has been pushed to the proximal direction until the first and the second connecting elements 15, 16 come into contact. The second connecting element 16 is pressed against the spring retainer 20, which is deformed in a way that it unlatches from the protrusions 26 and release the compressed spring 19. In this embodiment the vacuum connection between the first and second connecting elements 15,16 is not necessary for the retraction of the needle 9 due to the proximal position of the retraction spring 19. However, the change of shape of the second connecting element 16 is required in order to trigger the release of the spring retainer 20.

FIG. 6c schematically shows a cross-section of the ending step of use of the drug delivery device 1. The plunger 5 has now been pushed back by the spring 19 into the proximal direction until the whole needle assembly 8 and the whole needle 9 have been moved back with respect to the body unit 2 until they are completely housed by the body unit 2. A further mechanism (not shown) can now be used in order to prevent the needle 9 moving in a proximal direction following further pressing of the plunger 5. For example, features could be included to deliberately misalign the retracted needle with the second opening 4.

Figure 7:
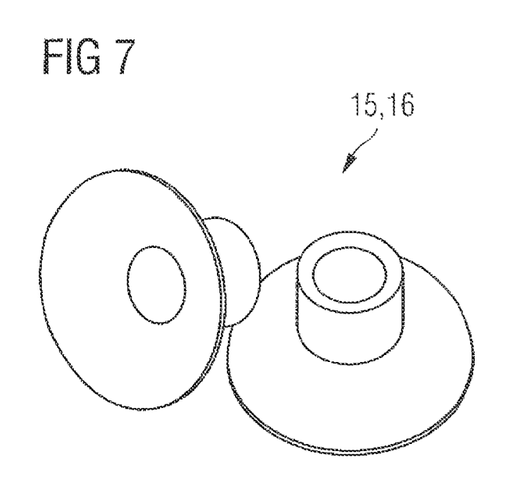
FIG. 7 shows a schematic picture of an embodiment of the first and/or second connecting element.

FIG. 7 shows a schematic picture of an embodiment of a connecting element. The connecting element shown in FIG. 7 could, for example, be used for the first connecting element 15 and/or for the second connecting element 16. In this embodiment, which is shown in the picture, the connecting element is a bung. The bungs could be made of rubber, for example.

Figure 8A:
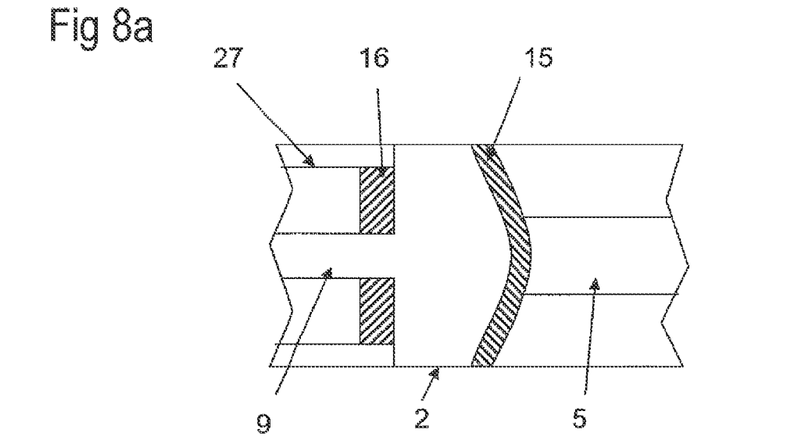
FIG. 8a-c show a schematic cross-section of another embodiment of the drug delivery device in three different steps of use.
Figure 8B:
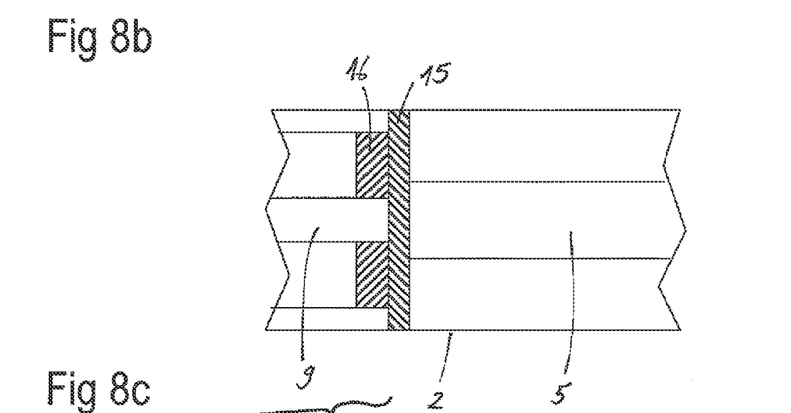
Figure 8C:
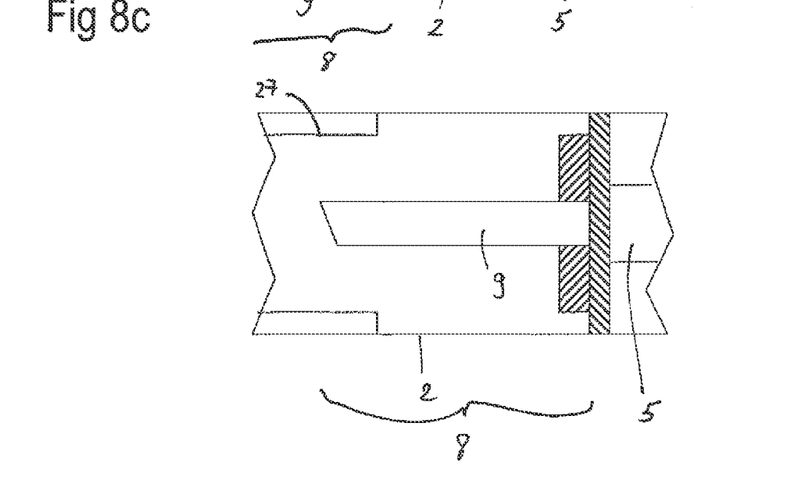

FIGS. 8*a-c* show a schematic cross-section of an embodiment of the drug delivery device in a section. The three figures show the body unit 2 including a section of reduced internal diameter 27, a section of the needle 9 on the left side and a section of the plunger 5 on the right side. The second connecting element 16, which is located at the proximal end of the needle 9, is shown. The second connecting element 16 is formed planar in this embodiment. The second connecting element 16 is formed with a smaller diameter compared to both the diameter of the first connecting element 15 and to the main internal diameter of the body unit 2. The proximal end of needle 9 aligns with the second connecting element 16 in this embodiment. The first connecting element 15, which is located at the inner side of the plunger 5, is formed concavely in this embodiment. The first connecting element 15 is preferably made of a flexible material, it could be a bung for example.

The FIG. 8*b* shows the situation when then plunger 5 is moved to the distal direction with respect to the body unit 2. Now, the first connecting element 15 and the second connecting element 16 are in contact with each other and the proximal end of the needle 9 is hermetically or nearly hermetically sealed by a face seal to the surface of the first connecting element 15. This forms a vacuum connection between the first and second connecting elements 15,16. Therefore, the plunger 5 and the needle assembly 8 are now engaged by means of the vacuum connection.

The FIG. 8*c* shows the situation when then plunger 5 is moved to the proximal direction with respect to the body unit 2. The vacuum connection causes the needle assembly 8 of needle 9 and second connection element 16 to move in the proximal direction drawing the needle into the body unit 2. As the second connection element 16 moves proximally into the body unit 2 quickly reaches a position where it is no longer in contact with the section of the body unit 2 with reduced internal diameter 27. The diameter of the second connection element 16 is smaller than that of the main diameter of the body unit 2. Therefore, once the second connection element 16 has ceased to contact the section of reduced internal diameter 27, the body unit 2 offers no further resistance to the proximal movement of the second connection element 16 and the needle 9. This offers a significant advantage compared, for example, to the embodiment shown in FIG. 3*a/b*, that the force required to draw the needle 9 into the body unit 2 is greatly reduced. A further advantage of this reduction in force is that there is now no force working against the vacuum connection between the first and second connecting elements 15,16. This significantly reduces the risk that the vacuum connection will fail.

LIST OF REFERENCES 1) drug delivery device
2) body unit
3) first opening
4) second opening
5) plunger
6) proximal end
7) distal end
8) needle assembly
9) needle
10) inner surface
11) channel
12) outer surface
13) proximal end
14) distal end
15) first connecting element
16) second connecting element
17) liquid
18) sleeve
19) spring
20) spring retainer
21) sleeve snap arms
22) plunger rod latch arms
23) sleeve latch features
24) recesses
25) plunger rod snap arms
26) protrusion
27) reduced internal diameter section

The invention claimed is:

1. Drug delivery device, comprising:
a body unit having a first opening and a second opening,
a plunger arranged such that its distal end is positioned inside the body unit, wherein the distal end of the plunger has a first connecting element, and wherein the plunger is moveable in the distal direction with respect to the body unit,
a needle assembly, with a proximal end and a distal end comprising a needle, wherein the proximal end of the needle assembly and the distal end of the plunger are configured such that they can get into a vacuum connection, and wherein the needle assembly has a second connecting element located at its proximal end
wherein, by being pressed together, the first and the second connecting element get into a vacuum connection combining the needle assembly with the plunger.

2. Drug delivery device according to claim 1, wherein at least one of the first and the second connecting elements is a bung.

3. Drug delivery device according to claim 1, wherein at least one of the first and the second connecting elements is elastic and concave towards the respective other element.

4. Drug delivery device according to claim 1, wherein one of the first and the second connecting element is elastic and convex towards the respective other element.

5. Drug delivery device according to claim 1, wherein at least one of the first and the second connecting elements is rigid and planar.

6. Drug delivery device according to claim 1, wherein the needle assembly is configured to be at least partly drawn back into the body unit, when the plunger is retracted.

7. Drug delivery device according to claim 1, wherein the drug delivery device is configured such that the needle does not move with respect to the body unit, when the needle assembly gets into the vacuum connection with the plunger.

8. Drug delivery device according to claim 1, wherein the proximal end of the needle is aligned with the second connecting element.

9. Drug delivery device according to claim 1, wherein the proximal end of the needle protrudes from the second connecting element in the direction of the plunger.

10. Drug delivery device according to claim 1, wherein the first connecting element is configured to seal hermetically with the proximal end of the needle.

11. Drug delivery device according to claim 1, wherein the first connecting element is configured to get into a vacuum connection with the second connecting element.

12. Drug delivery device according to claim 1, wherein the second connecting element is initially located in a position in contact with the inner surface of body unit and is moveable in proximal direction with respect to the body unit to a position where it is no longer in contact with the inner surface of the body unit.

13. Drug delivery device according to claim 1, comprising a medicament.

* * * * *

UNITED STATES PATENT AND TRADEMARK OFFICE
CERTIFICATE OF CORRECTION

PATENT NO. : 8,617,121 B2  Page 1 of 1
APPLICATION NO. : 13/202467
DATED : December 31, 2013
INVENTOR(S) : Lanin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 19 days.

Signed and Sealed this
Twenty-second Day of September, 2015

Michelle K. Lee
*Director of the United States Patent and Trademark Office*